(12) United States Patent
Menne et al.

(10) Patent No.: US 8,034,004 B2
(45) Date of Patent: Oct. 11, 2011

(54) MEDICAL DEVICE FOR THE TREATMENT OF BIOLOGICAL TISSUE

(75) Inventors: Andreas Menne, Signy (CH); Manfred Schulz, Ueberlingen (DE); Gerald Haupt, Kerpen (DE)

(73) Assignee: Ferton Holding S.A., Delemont (CH)

( * ) Notice: Subject to any disclaimer, the term of this patent is extended or adjusted under 35 U.S.C. 154(b) by 689 days.

(21) Appl. No.: 10/510,492

(22) PCT Filed: Apr. 1, 2003

(86) PCT No.: PCT/EP03/03373
§ 371 (c)(1),
(2), (4) Date: May 23, 2005

(87) PCT Pub. No.: WO03/084608
PCT Pub. Date: Oct. 16, 2003

(65) Prior Publication Data
US 2005/0209586 A1 Sep. 22, 2005

(30) Foreign Application Priority Data

Apr. 8, 2002 (DE) .................. 102 15 416

(51) Int. Cl.
*A61H 1/00* (2006.01)
*A61B 8/14* (2006.01)
(52) U.S. Cl. ............. 601/4; 601/2; 600/439; 600/459
(58) Field of Classification Search ........... 600/437, 600/439; 601/2–4; 606/1, 2.5, 127–128; 604/22
See application file for complete search history.

(56) References Cited

U.S. PATENT DOCUMENTS

| 3,499,437 | A | * | 3/1970 | Balamuth | 601/2 |
|---|---|---|---|---|---|
| 4,095,667 | A | * | 6/1978 | Mahig et al. | 181/120 |
| 4,530,360 | A | * | 7/1985 | Duarte | 607/51 |
| 4,549,535 | A | * | 10/1985 | Wing | 601/108 |
| 4,637,489 | A | * | 1/1987 | Iwanaka et al. | 181/160 |
| 4,674,505 | A | * | 6/1987 | Pauli et al. | 601/4 |
| 4,697,588 | A | * | 10/1987 | Reichenberger | 601/4 |
| 4,716,890 | A | * | 1/1988 | Bichel | 601/108 |
| 4,718,421 | A | * | 1/1988 | Rohwedder et al. | 601/4 |
| 4,727,875 | A | * | 3/1988 | Dory | 601/4 |
| 4,748,971 | A | * | 6/1988 | Borodulin et al. | 601/4 |
| 4,972,826 | A | * | 11/1990 | Koehler et al. | 601/4 |
| 5,160,336 | A | * | 11/1992 | Favre | 606/128 |
| 5,529,572 | A | * | 6/1996 | Spector | 601/2 |
| 5,540,702 | A | * | 7/1996 | Walz | 606/128 |

(Continued)

FOREIGN PATENT DOCUMENTS

FR 455868 8/1913

(Continued)

*Primary Examiner* — Long V. Le
*Assistant Examiner* — Angela M Hoffa
(74) *Attorney, Agent, or Firm* — Miles & Stockbridge P.C.; David R. Schaffer, Esq.; Michael A. Minter, Esq.

(57) ABSTRACT

Disclosed is a medical instrument for treating biological tissue, comprising a device generating extracorporeal pressure waves and a transmission element (2) coupling said pressure waves into the body of living beings. The pressure wave is generated by a stroking member (10) impacting on a transmission element (2) and is transmitted inside the transmission element. Said transmission element comprises a boundary surface at the outlet thereof, which is curved towards the inside and is configured such that the pressure waves can be coupled into the biological tissue and can be focused therein.

20 Claims, 5 Drawing Sheets

U.S. PATENT DOCUMENTS

| | | | |
|---|---|---|---|
| 5,545,124 A * | 8/1996 | Krause et al. | 601/2 |
| 5,618,275 A * | 4/1997 | Bock | 604/290 |
| 5,727,556 A * | 3/1998 | Weth et al. | 600/439 |
| 5,868,756 A * | 2/1999 | Henry et al. | 606/128 |
| 6,036,661 A * | 3/2000 | Schwarze et al. | 601/4 |
| 6,068,596 A * | 5/2000 | Weth et al. | 600/437 |
| 6,217,530 B1 * | 4/2001 | Martin et al. | 601/2 |
| 6,312,434 B1 * | 11/2001 | Sutrina et al. | 606/127 |
| 6,413,230 B1 * | 7/2002 | Haupt et al. | 601/2 |
| 6,736,784 B1 * | 5/2004 | Menne et al. | 601/2 |
| 6,875,220 B2 * | 4/2005 | Du et al. | 606/169 |
| 2003/0199857 A1 * | 10/2003 | Eizenhofer | 606/2.5 |

FOREIGN PATENT DOCUMENTS

WO      WO 9857707 A1 * 12/1998

\* cited by examiner

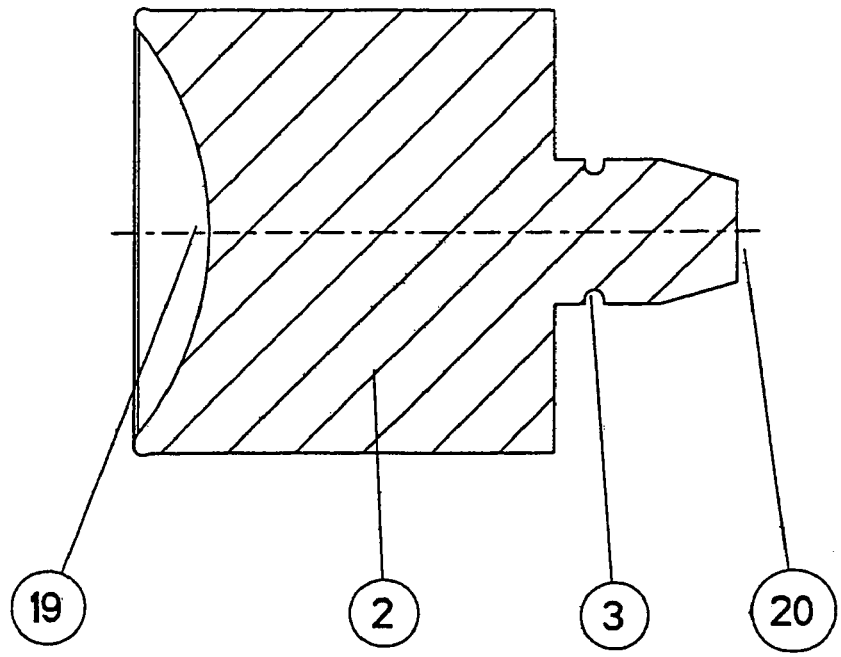
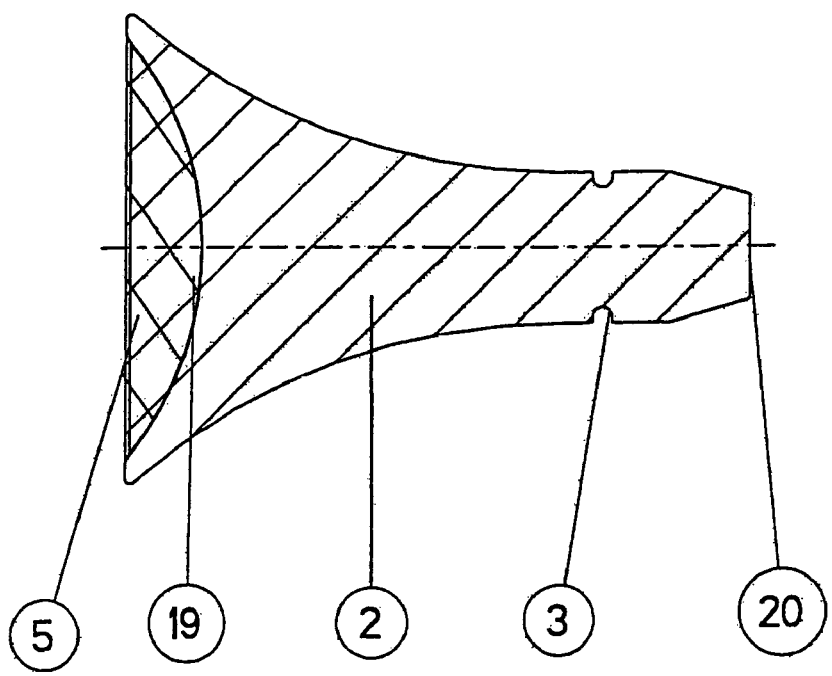

MEDICAL DEVICE FOR THE TREATMENT OF BIOLOGICAL TISSUE

BACKGROUND OF THE INVENTION

The invention relates to a medical instrument for the treatment of biological tissue.

Such instruments are used to accelerate or even initiate the process of healing broken bones and bone defects, but also paradontosis, by means of pressure or impact waves. Other fields of application are the treatment of chronic pains occurring with disorders of the point of attachment of sinews and the dissolution of myofascial trigger areas. It is assumed that the pressure waves cause microscopic damages to the biological tissue that cause the body to take regenerating actions.

Presently, so-called extracorporeal pressure or impact wave devices are used for such applications. These devices generate an acoustic pulse and pass it, via the skin surface, to the target region within the body, where it will then become effective. A device of this class of apparatus, which has a simple structure, is described in the patent document DE 197 25 477. Here, the acoustic pulse is generated by the impact of a projectile and is coupled unfocussed into the body via a blunt transmission element. Other medical devices of this type focus an acoustic pulse to the target region. A typical example of such a device can be found in the German Laid Open document DE 23 51 247. Here, a spark discharge serves as the source of the acoustic pulse which is focused by an elliptic reflector. For generating the pressure waves, prior art meanwhile also includes electromagnetic and piezoelectric sources (DE 35 02 751). Known alternative means for focusing are the use of acoustic liquid or solid matter lenses (U.S. Pat. No. 5,727,875), the design of the acoustic source as a moved spherical cap surface (DE 33 12 014 C2) or the disposition of a plurality of sources on a ball surface (DE 199 28 491 A1) as they are often used in piezoelectric drives.

The operation of all known focusing systems requires a high voltage power unit to generate the short but strong acoustic pulses. This makes the devices complicated, limits the maximum repetition frequency per unit time with a still reasonable structural size, and requires safety measures for isolating the high voltage. The embodiments of DE 197 25 477 do not allow a focusing of the acoustic energy and applications are thus restricted to indications close to the surface.

SUMMARY OF THE INVENTION

Thus, it is the object of the invention to provide a pressure or impact wave device such that it generates pressure or impact waves in a simple and economic manner and focuses these waves onto a target region in the body.

Advantageously, the invention comprises a primary pressure wave generator, wherein an impact member may be accelerated to a high final velocity through a drive means and exerts an impulse on a transmission element. Due to this impulse, the impact member induces a pressure wave in the transmission element, which propagates therein towards its exit boundary surface from where it is coupled into the biological tissue. The exit boundary surface is designed such that the exiting wave forms a focus in the biological tissue. This is achieved by the shaping of the transmission element, wherein the propagation time from the generation by the impulse to the focus is the same for each local wave. In a first approximation, an almost spherical exit boundary surface would be obtained for a straight transmission element of steel.

Preferably, the impact member is a projectile of metal or another high-strength material, which may be reciprocated in a guiding by means of a pulse of compressed air. Due to its simplicity and the weight advantages, the pneumatic drive is particularly suited to accelerate the impact member to a high final velocity and the accompanying high impulse energies. However, other drives using a spring mechanism or electromagnetic means are contemplated.

Especially in orthopaedic applications, it is advantageous to couple a plurality of individual pulses into the biological tissue to obtain an optimum effect. Therefore, the drive means is preferably designed such that a periodic reciprocating movement of the impact member is possible. The impact frequency is approximately 1 to 30 Hz, preferably 5 to 12 Hz. With pulse numbers of about 2000 per session, as presently recommended for orthopaedic applications, treatment times of less than five minutes are possible.

In a preferred embodiment, the transmission element is guided linearly and axially in a housing, a spring/damping element being arranged between the transmission element and the housing. In this manner, a decoupling of the transmission element is realized. Moreover, the spring/damping element returns the transmission element to its initial position after each individual pulse and limits the movement of its center of gravity. Further, the spring/damping element seals the exterior space from the interior part and prevents the intrusion of dirt. For coupling the pressure or impact wave into the biological tissue, a great deflection of the transmission element is not necessary and is not desirable, since it is particularly painful to the patients. Rather, the wave transmission is effected by compressing and expanding the transmission element and not by its displacement. Therefore, typical values for the stroke of the transmission element are less than 0.5 mm.

An intermediate element may be provided between the impact member and the transmission element, which passes the impulse from the impact member to the transmission element. This intermediate element can serve to achieve a better shielding of the drive means from the application area or to redirect the direction of the pressure wave or to influence the pressure wave characteristics.

Preferably, the transmission element is made of a high-strength material, such as steel, to stand the stresses caused by the action of the impact member. In a preferred embodiment, the impacting surface of the impact member and the surface of the transmission element that is hit are planar and oriented perpendicular to the direction of movement of the impact member. In such a case, the impact creates a planar wave in the transmission element that propagates within the same. When the transmission element is a bolt without substantial variations in cross section, the wave retains its shape and wanders towards the exit boundary surface as an planar wave. The preferred exit boundary surface of the transmission element has almost the shape of an inwardly curved ball surface. In this case, there is a point in the biological tissue where—due to the different speeds of sound in the transmission element and in the biological tissue—all individual local waves arrive at the same time, thus forming a focus. The position of the focus in the biological tissue with respect to the transmission element can be preset by the selection of the radius of curvature of the exit boundary surface. The ideal geometry of the exit boundary surface differs slightly from a ball surface and can be determined by calculation.

To increase the emitted acoustic power of the transmission element, its exit boundary surface should be chosen as large as possible, whereas the diameter of the impact member should be kept as small as possible, so as to make the moved masses and pulses manageable for a medical application. It has been found that, when the diameters of the impact member and the exit area of the transmission element are the same, the possibility of focusing is limited.

For an optimum generation of the pressure wave in the transmission element, the impact surface of the impact member and the entry surface of the transmission member should be chosen to be of equal size. In a preferred embodiment, the exit diameter of the transmission element should thus be dimensioned larger than the transverse dimension of the impact member or its own entry diameter, respectively.

Therefore, the transmission element is preferably formed as an exponential horn that provides for a loss-free transition of the planar wave from small cross sections to larger ones. Neglecting the ideal transmission, other optional enlargements of the cross section of the transmission element from its entry diameter to the exit diameter are possible. The geometry of the exit boundary surface of the transmission element should then again be chosen such that the propagation times of the wave form a focus in the biological tissue.

With such transmission elements, the outer edges, formed by the inwardly curved exit boundary surface, protrude. Since a movement of the transmission element due to the impact pulse cannot be avoided completely, these protruding edges may damage or at least irritate the biological tissue. Therefore, in a preferred embodiment, these outer edges are formed atraumatic. Rounding the edges or providing a protective coating are suitable measures. It is also conceivable that the outer edges of the housing slightly protrude in the axial direction so that the transmission element will not come into direct contact with the biological tissue.

An impedance adjustment medium may be arranged between the exit boundary surface and the point of coupling on the biological tissue, the medium improving the coupling of the pressure wave into the biological tissue. When entrapped air is present between the exit boundary surface of the transmission element and the entry surface of the biological tissue, a part of the pressure pulse is reflected at this acoustic irregularity and the portion transmitted is reduced. A suitable paste-like impedance adjustment medium is, e.g., an ultrasound gel or another pasty mass with an impedance similar to that of the biological tissue (e.g. Vaseline).

To avoid air entrapments, the cavity formed by the spherical shape may be lined with a solid, acoustically well conductive material. Such a suitable material is polystyrene, for example.

BRIEF DESCRIPTION OF THE DRAWINGS

FIGS. 3 to 8 illustrate a series of different embodiments of a transmission element.

DESCRIPTION OF THE PREFERRED EMBODIMENTS

Figure 1:
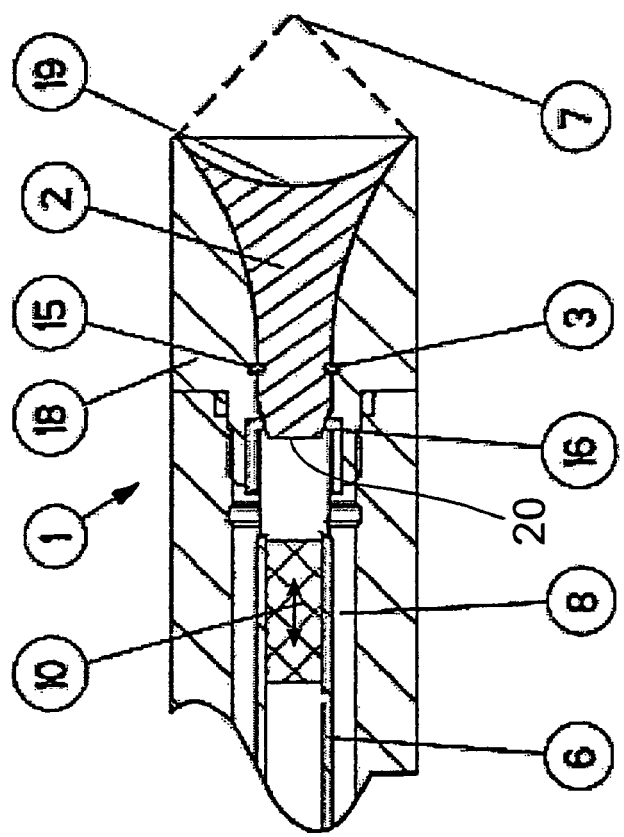
FIGS. 1 and 2 illustrate a mechanically operated medical device in cross section.
Figure 1:
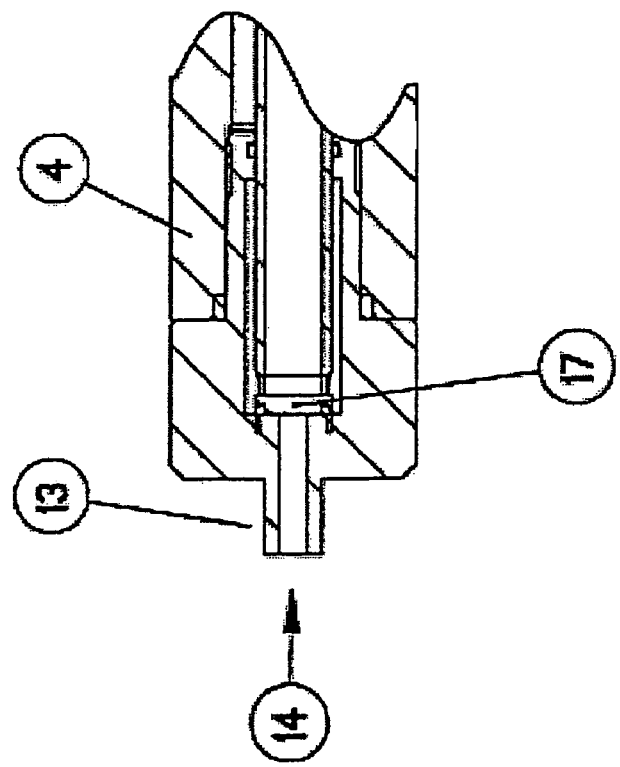

The handpiece 1 illustrated in FIG. 1 consists of a housing 4 accommodating a pneumatic inner cylinder 6 in which an impact member 10 is reciprocated between two end positions using pneumatic drive means 14 in combination with a dynamic pressure chamber 8 coaxially surrounding the inner cylinder 6 in an annular manner. As an alternative, the impact member 10 may be moved hydraulically, mechanically, electromagnetically or by other drive means. Depending on the type of drive, a suitable length of the acceleration path can be chosen. For a pneumatically operated impact unit and a typical compressed air pressure of about 0.3 MPa (3 bar), the acceleration path is about 50 to 200 mm. The length, the final velocity and the material composition of the impact member 10 may be selected in order to characterize the pressure or impact wave. Typically, the power of the medical instrument is set by regulating the compressed air by means of a pressure reducing means.

In the proximal end position of the impact member 10, a magnetic holder 17 is provided at the end of the inner cylinder 6, which can hold the metal impact member 10 in its proximal end position until pneumatic pressure applied via the connection 13 again accelerates the impact member 10 towards the distal end of the inner cylinder 6. The air present in the direction of movement of the impact member 10 is guided into the dynamic pressure chamber 8 via annular slits 16 in the distal end of the inner cylinder 6. Due to the acceleration, the impact member 10 hits the entry boundary surface 20 of a transmission element 2, which is located distally of the inner cylinder 6, with a high final velocity of 10 to 25 m/sec, for example, and induces a pressure or impact wave therein that propagates to its exit boundary surface 19 and is then coupled into the biological tissue. The transmission element 2 is made of a metallic material and is slidably guided in a receptacle 18. An annular groove 3 is provided in the transmission element 2 and in the receptacle 18, an elastic spring/damping element 15 being situated in the groove. This element serves to decouple the transmission element 2 from the receptacle 18, but also has the effect that the transmission element 2 returns to its initial position after the impact. At the same time, the spring/damping element 15 seals the pressure chamber 8 from the exterior space and thus prevents the compressed air from escaping and dirt from intruding. The exit boundary surface 19 of the transmission element 2 is formed as a section of a spherical surface. In a first approximation, the focus 7 of the exiting pressure or impact wave corresponds to the geometric center of the spherical surface.

After the termination of the impact action, the spring/damping element 15 returns the transmission element 2 into its initial position. The impact member 10 is returned into its rest position at the proximal end of the inner cylinder 6 by the overpressure built up in the dynamic pressure chamber 8 and the return flow of the air through the annular slits 16, and is fixedly held by the magnetic holder 17. The instrument is then prepared for another impact action.

Figure 2:
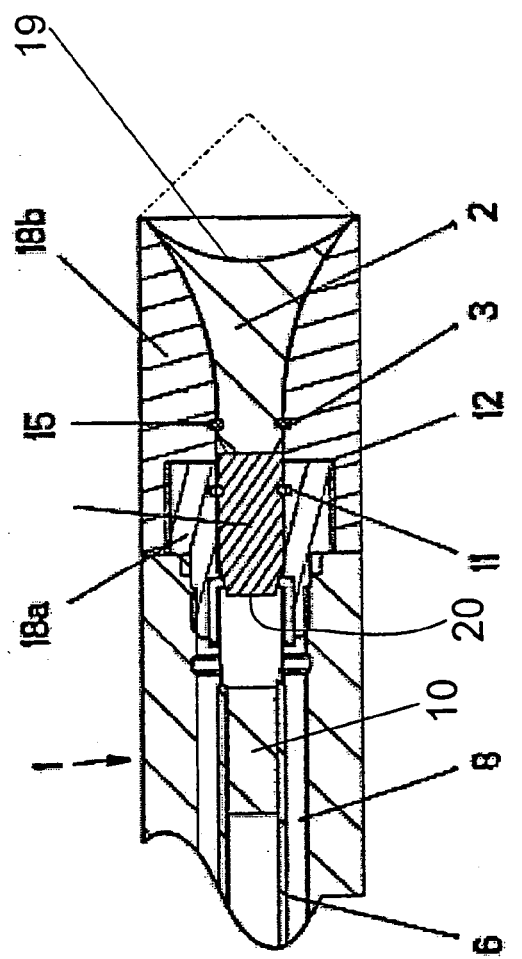
Figure 2:
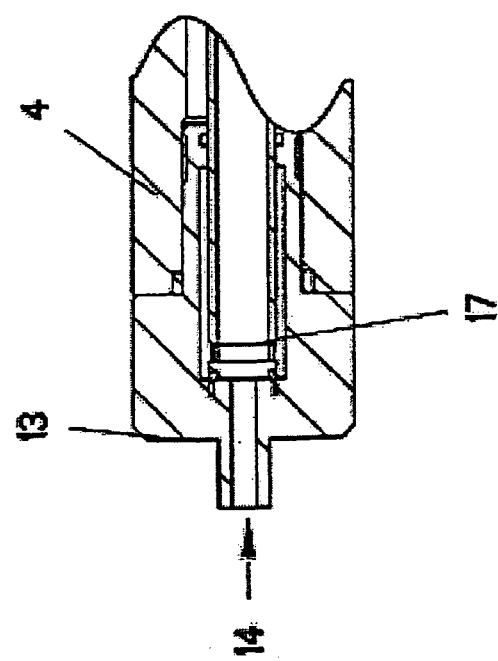

The embodiment illustrated in FIG. 2 is additionally provided with an intermediate member 9 with a seal 11, which is arranged between the impact member 10 and the transmission element 2. This component is intended to be hit by the impact member 10 and to pass the impact pulse to the transmission element 2. Here, the receptacle 18a and 18b is of two-piece structure. By loosening the rotary connection 12, the transmission element 2 and the front receptacle 18 can be removed. The handpiece 1 remains closed in the process and is easily cleaned, disinfected and sterilized, without liquid or dirt being able to enter the interior of the handpiece 1.

Figure 3:
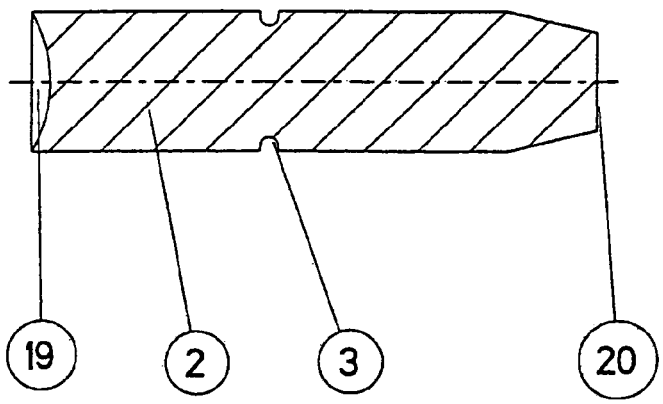

A transmission element 2 of very simple structure is illustrated in FIG. 3. In this case, an enlargement of the cross section has been omitted, so that the outer diameter of the transmission element remains constant.

Figure 4:
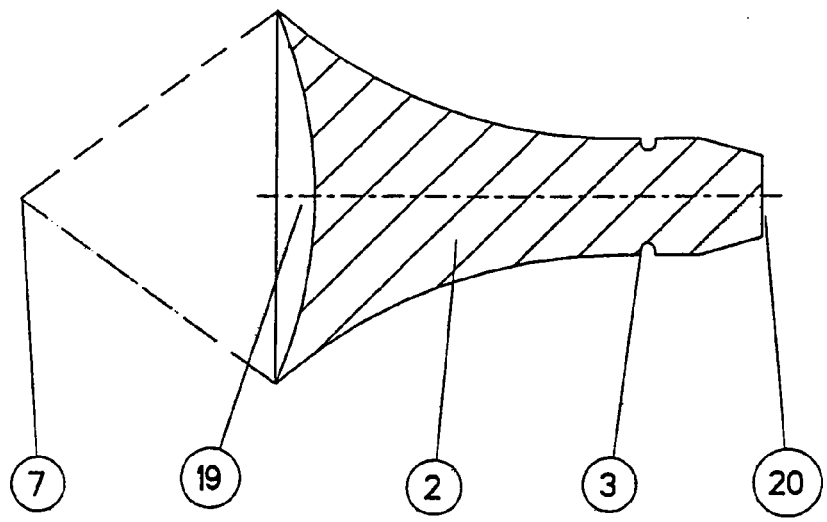
Figure 5:
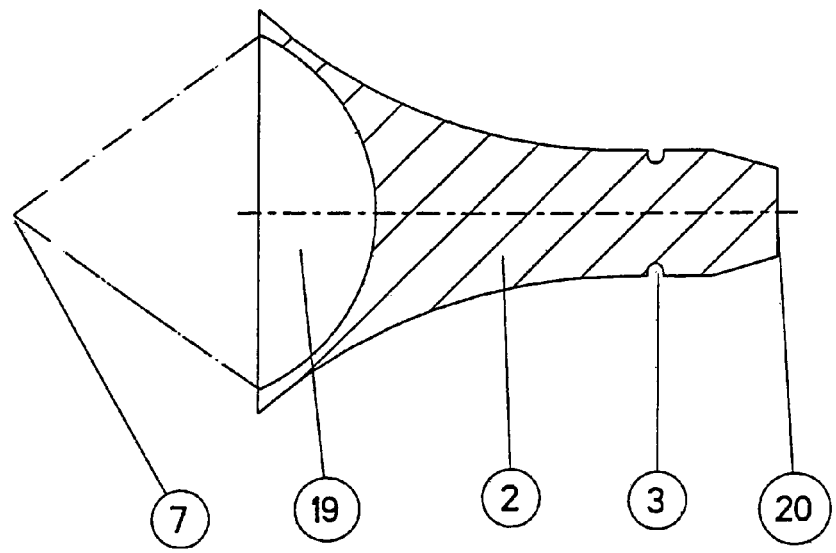

By varying the radius of curvature of the exit boundary surface 19 of the transmission element 2, the position of the focus 7 may be set. FIG. 4 illustrates a transmission element 2 with a large radius of curvature, whereby the focus 7 is situated farther behind the exit boundary surface 19. FIG. 5 illustrates an embodiment with a small radius of curvature.

Figure 6:
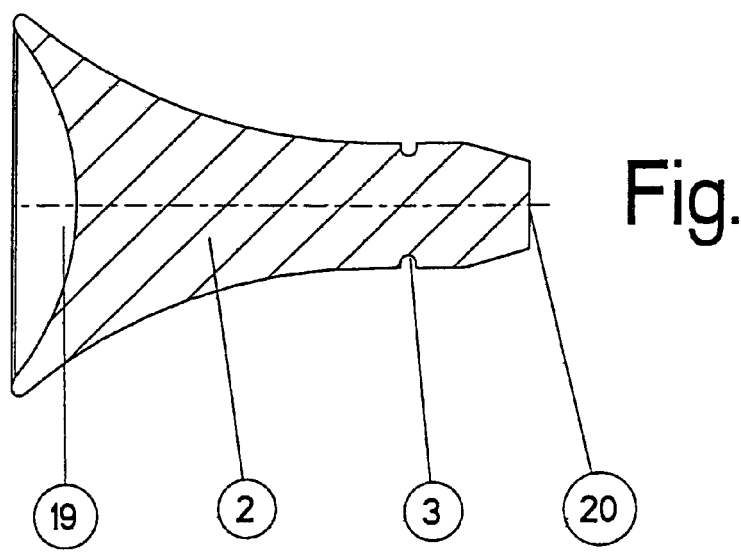

Due to the geometric shape of the exit boundary surface 19 of the transmission element 2, sharp edges are formed that could lead to an injury or irritation of the biological tissue. For this reason, the outer edges of the transmission element 2 are rounded in FIG. 6.

For a simpler handling or for reasons of manufacturing costs, designing the enlarged cross section of the transmission element 2 from its entry diameter to its exit diameter as an exponential horn can be omitted, and a simple stepped transition can be used. FIG. 7 illustrates such an embodiment.

To avoid air entrapments and to obtain a planar surface of the transmission element 2, the spherical exit boundary surface 19 of the transmission element 2 is lined with an acoustically well conductive insert 5, as illustrated in FIG. 8, which has impedances similar to those of the biological tissue.

Although a preferred embodiment of the invention has been specifically illustrated and described herein, it is to be understood that minor variations may be made in the apparatus without departing from the spirit and scope of the invention, as defined by the appended claims.

We claim:

1. A medical instrument adapted for the treatment of biological tissue, comprising:
    an impact member (10) for generating extracorporeal pressure waves, and
    a transmission element (2) adapted to couple the pressure waves into the body of living beings,
    characterized in that the pressure waves are generated by the impact member (10) hitting the transmission element (2) and the pressure waves propagate in the transmission element (2),
    the transmission element (2) has an inwardly curved exit boundary surface (19) configured such that the transmission element (2) is adapted to be placed in contact with the biological tissue, and the pressure waves are adapted to then be coupled into the biological tissue and are adapted to then be focused in the biological tissue,
    the transmission element (2) is in the shape of an exponential horn, the transmission element (2) having a larger diameter at the exit boundary surface (19) than at an axially opposite entry boundary surface (20), and
    the exit boundary surface (19) of the transmission element (2) travels a stroke of less than 0.5 mm due to the impact member (10) hitting the entry boundary surface (20) of the transmission element (2).

2. The medical instrument as defined in claim 1, wherein the impact member (10) is guided in a housing and is adapted to be reciprocated by means of a drive means, the impact member (10) exerting one or more impulses on the transmission element (2) and inducing a pressure wave in the transmission element (2) due to the impulse, the pressure wave propagating to the exit boundary surface (19) of the transmission element (2).

3. The medical instrument as defined in claim 2, wherein the impact member (10) is arranged coaxially to the transmission element (2).

4. The medical instrument as defined in claim 1, wherein the pressure wave source may be driven periodically, the impact member (10) and the transmission element (2) being self-returnable.

5. The medical instrument as defined in claim 1, wherein the impact frequency of the impact member (10) is about 1 to 30 Hz.

6. The medical instrument as defined in claim 1, wherein a spring/damping element (15) is provided between the transmission element (2) and the housing (4).

7. The medical instrument as defined in claim 1, wherein an intermediate element (9) is arranged between the impact member (10) and the transmission element (2), which intermediate element passes an impulse from the impact member (10) to the transmission element (2).

8. The medical instrument as defined in claim 1, wherein the outer edges of the exit boundary surface of the transmission element are rounded or provided with a protective coating.

9. The medical instrument as defined in claim 1, wherein an impedance-adjusting medium (5) is adapted to be provided between the exit boundary surface (19) of the transmission element (2) and the biological tissue for improving the coupling of the pressure wave into the biological tissue.

10. The medical instrument as defined in claim 1, wherein the impact frequency of the impact member (10) is about 1 to 12 Hz.

11. A medical instrument for the treatment of biological tissue by generating extracorporeal pressure waves and adapted to couple the pressure waves into the body of living beings, comprising:
    an impact member (10) for hitting against an entry boundary face (20) of a transmission element (2) thereby generating extracorporeal pressure waves which are propagated in and travel through the transmission element (2) from the entry boundary face (20) thereof to an opposite remote inwardly curved exit boundary surface (19) configured such that the transmission element (2) is adapted to be placed in contact with the biological tissue, and the pressure waves are adapted to then be coupled into and focused relative to the biological tissue, and
    impedance-adjusting means (5) provided contiguous the inwardly curved opening exit boundary surface (19) of the transmission element (2), adapted for improving the coupling of the pressure wave into the biological tissue,
    wherein the exit boundary surface (19) of the transmission element (2) travels a stroke less than 0.5 mm due to the impact member (10) hitting the entry boundary face (20) of the transmission element (2), and
    wherein the transmission element (2) is in the shape of an exponential born, and the transmission element (2) has a larger diameter at the exit boundary surface (19) than at the entry boundary face (20).

12. The medial instrument as defined in claim 11 wherein the impedance-adjusting means (5) is an acoustically conductive medium located substantially within the entirety of the inwardly curved exit boundary surface (19).

13. A medical instrument for the treatment of biological tissue, comprising:
    an impact member(10) for generating extracorporeal pressure waves, and
    a transmission element (2) adapted to couple the pressure waves into the body of living beings,
    wherein the impact member (10) is configured to generate the pressure waves by hitting a transmission element (2) and the pressure waves propagate in the transmission element (2);
    the transmission element (2) has an inwardly curved exit boundary surface (19) configured such that the transmission element (2) is adapted to be placed in contact with the biological tissue, and the pressure waves are adapted to then be coupled directly into the biological tissue and are adapted to then be focused directly in the biological tissue;
    the transmission element (2) is formed in the shape of an exponential horn, the transmission element (2) having a larger diameter at the exit boundary surface (19) than at an axially opposite entry boundary surface (20); and the transmission element (2) is formed such that the transmission element (2), the entry boundary surface (20), and the exit boundary surface (19) constitute a one-piece body.

14. The medical instrument as defined in claim 13, wherein the impact member (10) is guided in a housing and is adapted to be reciprocated by means of a drive means, the impact member (10) exerting one or more impulses on the transmission element (2) and inducing a pressure wave in the transmission element (2) due to the impulse, the pressure wave propagating to the exit boundary surface (19) of the transmission element (2).

15. The medical instrument as defined in claim 13, wherein the impact frequency of the impact member (10) is in the range of 1 to 30 Hz.

16. The medical instrument as defined in claim 13, wherein a spring/damping element (15) is provided between the transmission element (2) and the housing (4).

17. The medical instrument as defined in claim 13, wherein the exit boundary surface (19) of the transmission element (2) travels a stroke of less than 0.5 mm due to the impact member (10) hitting the transmission element (2).

18. The medical instrument as defined in claim 13, wherein an intermediate element (9) is arranged between the impact member (10) and the transmission element (2), which intermediate element passes an impulse from the impact member (10) to the transmission element (2).

19. The medical instrument as defined in claim 13, wherein an impedance-adjusting means (5) is adapted to be provided between the exit boundary surface (19) of the transmission element (2) and the biological tissue for improving the coupling of the pressure wave into the biological tissue, and wherein the impedance-adjusting means (5) is an acoustically conductive medium located substantially within the entirety of the inwardly curved exit boundary surface (19).

20. The medical instrument as defined in claim 13, wherein the impact frequency of the impact member (10) is in the range of 1 to 12 Hz.

* * * * *